United States Patent
Wimmer et al.

(10) Patent No.: US 10,486,209 B2
(45) Date of Patent: Nov. 26, 2019

(54) METHOD AND DEVICE FOR RECYCLING METAL SCRAP

(71) Applicants: Michael Wimmer, Köln (DE); Ronald Gillner, Swisttal (DE); Nils Robert Bauerschlag, Aachen (DE); Thomas Roß, Düsseldorf (DE)

(72) Inventors: Michael Wimmer, Köln (DE); Ronald Gillner, Swisttal (DE); Nils Robert Bauerschlag, Aachen (DE); Thomas Roß, Düsseldorf (DE)

(73) Assignee: Hydro Aluminium Rolled Products GmbH, Grevenbroich (DE)

( * ) Notice: Subject to any disclaimer, the term of this patent is extended or adjusted under 35 U.S.C. 154(b) by 0 days.

(21) Appl. No.: 16/005,023

(22) Filed: Jun. 11, 2018

(65) Prior Publication Data

US 2018/0297091 A1    Oct. 18, 2018

Related U.S. Application Data

(63) Continuation of application No. PCT/EP2016/082112, filed on Dec. 21, 2016.

(30) Foreign Application Priority Data

Dec. 23, 2015    (DE) .................. 10 2015 122 818

(51) Int. Cl.
B07C 5/34       (2006.01)
B09B 3/00       (2006.01)
(Continued)

(52) U.S. Cl.
CPC .................. *B09B 3/00* (2013.01); *B07C 5/00* (2013.01); *B07C 5/34* (2013.01); *B07C 5/346* (2013.01);
(Continued)

(58) Field of Classification Search
CPC ....... B07C 5/3416; B07C 5/344; B07C 5/346; B07C 5/38; B07C 2501/0054; C22B 1/005; C22B 7/005; C22B 21/0069
See application file for complete search history.

(56) References Cited

U.S. PATENT DOCUMENTS

| | | | |
|---|---|---|---|
| 4,317,521 A | | 3/1982 | Clark et al. |
| 5,180,421 A | * | 1/1993 | Rostoker ................. B09B 3/005 75/323 |
| 5,396,071 A | * | 3/1995 | Atwell .................. G01N 23/222 198/811 |
| 5,813,543 A | | 9/1998 | Gesing et al. |

(Continued)

FOREIGN PATENT DOCUMENTS

| | | |
|---|---|---|
| DE | 102012024816 B4 | 4/2014 |
| DE | 102014013160 A1 | 3/2016 |

(Continued)

*Primary Examiner* — Joseph C Rodriguez
(74) *Attorney, Agent, or Firm* — Reinhart Boerner Van Deuren P.C.

(57) ABSTRACT

A method for recycling metal scraps, particularly aluminum scraps, is provided. In the method, an amount of metal scrap, particularly aluminum scrap, is provided in the form of a plurality of separated split lots. A composition analysis is carried out for each split lot and an item of composition information based on said composition analysis is associated with each split lot that has been analyzed. Also provided is a device configured for carrying out said method.

14 Claims, 5 Drawing Sheets

(51) Int. Cl.
*B07C 5/00* (2006.01)
*B07C 5/346* (2006.01)
*B09B 5/00* (2006.01)
*C22C 21/00* (2006.01)
*C22B 1/00* (2006.01)
*C22B 7/00* (2006.01)
*C22B 21/00* (2006.01)
*G01N 21/71* (2006.01)
*G01N 23/222* (2006.01)
*G01N 23/223* (2006.01)

(52) U.S. Cl.
CPC .............. *B07C 5/3412* (2013.01); *B09B 5/00* (2013.01); *C22B 1/005* (2013.01); *C22B 7/005* (2013.01); *C22B 21/0069* (2013.01); *C22C 21/00* (2013.01); *G01N 21/718* (2013.01); *G01N 23/222* (2013.01); *G01N 23/223* (2013.01); *G01N 2223/643* (2013.01); *Y02P 10/212* (2015.11)

(56) References Cited

U.S. PATENT DOCUMENTS

| | | | | |
|---|---|---|---|---|
| 5,948,137 | A * | 9/1999 | Pflaum | C21C 5/4673 266/100 |
| 5,959,870 | A * | 9/1999 | Hurwitz | G01N 23/222 198/508 |
| 6,266,390 | B1 | 7/2001 | Sommer, Jr. et al. | |
| 6,545,240 | B2 * | 4/2003 | Kumar | B07C 5/3425 209/579 |
| 6,579,339 | B1 * | 6/2003 | Jamison | C22B 15/0056 75/386 |
| 7,253,414 | B2 * | 8/2007 | Osucha | G01N 23/12 250/358.1 |
| 7,886,915 | B2 * | 2/2011 | Shulman | B07C 5/344 209/552 |
| 9,956,609 | B1 * | 5/2018 | De Saro | B22D 47/00 |

FOREIGN PATENT DOCUMENTS

| | | | | |
|---|---|---|---|---|
| EP | | 0096092 A1 | 12/1983 | |
| FR | | 2562913 A1 | 10/1985 | |
| WO | WO 2013/020712 A1 | | 2/2013 | |
| WO | WO-2017109035 A1 * | | 6/2017 | ............... B07C 5/02 |

* cited by examiner

METHOD AND DEVICE FOR RECYCLING METAL SCRAP

CROSS-REFERENCE TO RELATED PATENT APPLICATIONS

This patent application is a continuation of PCT/EP2016/082112, filed Dec. 21, 2016, which claims priority to German Application No. 10 2015 122 818.1, filed Dec. 23, 2015, the entire teachings and disclosure of which are incorporated herein by reference thereto.

FIELD OF THE DISCLOSURE

The invention relates to a method and a device for recycling metal scraps, particularly aluminium scraps.

BACKGROUND OF THE DISCLOSURE

In the production and processing of aluminium strips, production scraps accumulate at different collection points. It is desirable to use these production scraps in a recirculation by melting again for the production of the product, in the production of which they accrue. It is also desirable to use the post production scraps again for the production of products of the same or similar alloys, so that also in the case of said scraps ultimately a recirculation is achieved. The post production scraps can be scraps, which accrue from aluminium products through use, consumption or wear and tear. The scraps may, for example, be provided by pressing plants.

Since in aluminium rolling mills typically different aluminium alloys are processed, it, however, frequently occurs that scraps of different alloys are mixed together. For a preferably performed recirculation such a mixture must, however, be excluded, since otherwise limit values for alloy elements in the case of a mixture of different production scraps cannot be complied with.

In order to identify a mixture, according to the current prior art samples of the accumulated scrap are taken and examined, typically 2 to 30 samples. However, in this connection, a significant statistical uncertainty concerning the actual composition of the scrap still exists, which is in particular too high for an efficient recirculation of the scraps.

If a mixture of scraps should remain undetected, that can lead to the entire melting furnace batch of up to 100 tonnes being outside of the specifications and in the worst case having to be scrapped.

Against this background the problem addressed by the present invention is to provide a method and a device for the recycling of metal scraps, particularly aluminium scraps, with which a more efficient recirculation of the scraps can be achieved.

BRIEF SUMMARY OF THE DISCLOSURE

This problem is solved at least partially according to the present invention by a method for the recycling of metal scraps, particularly aluminium scraps, in which an amount of metal scrap, particularly aluminium scrap, is provided in the form of a plurality of separated split lots and in which, for each split lot, a composition analysis is carried out and an item of composition information based on said composition analysis is assigned to the respective split lot that has been analysed.

The metal scrap, particularly aluminium scrap, can in particular be production scrap, that is, scrap, which accrues during the production operation, for example, trimming scrap from an edge trimming of a rolled aluminium strip.

In the method, an amount of metal scrap, particularly aluminium scrap, is provided in the form of a plurality of separated split lots. Separated split lots are understood to mean parts of the total scrap, which are stored separately from each other and thus can be kept apart. The split lots are preferably provided in the form of individual packages, in which the scrap of a split lot is respectively combined in a packing, for example, in a scrap container.

Preferably, the amount of scrap accumulated in a production operation is allocated to different scrap containers. In particular, a plurality of scrap containers may be provided, which scrap containers are filled one after the other with an amount of scrap. In this way, a scrap container in each case contains the scrap, which has accumulated in a specific time interval during the production operation.

In the method, a composition analysis is carried out for each split lot. For this purpose, the scrap of the split lot is subjected in particular to a chemical analysis, in order to determine the proportions (the contents) of one or a plurality of alloy elements contained in the scrap.

The analysis is performed in particular for the entire mass of the scrap and not only for individual samples, which would lead to a high degree of inaccuracy. The analysis of the entire mass of a split lot aims to identify impurities, so that an efficient recirculation of process scraps is made possible.

An item of composition information based on the composition analysis is assigned to the respective split lot that has been analysed. For example, values for the content of specific alloy elements (such as, for example, Fe, Si, Mn, Mg, etc.) may be assigned to the split lot.

The assignment can be performed by providing the split lot with a unique identification, for example, by labeling a scrap container which contains the split lot of scrap, and by linking the identification of the split lot in an electronic memory of a data processing system with the associated item of composition information, for example, in a table.

It is preferable for the recirculation of scraps, that the scraps are kept separate at the collection points, in order to prevent a mixture of different alloys. The separation of the scraps occurs at the collection points in small split lots or packages, respectively, with a mass of, for example, 100 to 2,500 kg. A mixture of scraps is, however, also not impossible in the small split lots or packages, respectively. Post production scraps, for example, from pressing plants of the automobile industry, can also exist in larger split lots of up to 15,000 kg.

The invention is based on the finding that a more efficient recirculation of the scrap can be achieved by combining a division of scrap into small split lots with a complete analysis of the scrap of the split lots. In this way, split lots that are contaminated by alien scrap can be identified and excluded in a targeted manner from a recirculation of the process scraps and can be used otherwise, preferably for another alloy, in particular aluminium alloy.

It was found that the division of the scrap into split lots already creates advantages, since in the production operation scraps of different alloys generally accrue one after another and therefore a separation of scraps of different alloys can already be achieved by filling several scrap containers one after another. However, it was also found that, in case of a product transitions in the production operation, a mixture of scraps of before and after the transition frequently occurs in individual scrap containers. By means of the complete analysis of the split lots it is possible to identify such mixtures reliably and to take them into consideration in the further use of the split lots.

The split lots preferably have in each case a mass in the range of 500 and 15,000 kg, preferably from 500 to 5000 kg, in particular from 1000 to 4000 kg.

In particular, practically the entire amount of scrap of a split lot is examined, so that a significantly higher reliability is achieved than with a sample-based analysis. If a contamination is found in a split lot (or in a container, respectively), this split lot/container is preferably not supplied to the recirculation, but rather is used otherwise, preferably for other aluminium alloys. Split lots/containers without contamination can be used for a recirculation. A contamination can be determined by determining the cumulative content of individual alloy elements of the entire amount of scrap of a split lot/container. If the content of one or of a plurality of alloy elements in the composition analysis exceeds, for example, a predetermined threshold value, a contamination must be assumed. Which alloy elements may not be exceeded depends on the product the scrap of which is recirculated.

The aforementioned problem is furthermore also at least partially solved according to the present invention by a device, configured or having respective means for carrying out the previously described method.

Different embodiments of the method and of the device are described below, wherein the individual embodiments in each case can be used both for the method as well as for the device and also can be freely combined with each other.

In a first embodiment, the composition analysis of a split lot is carried out in that the entire scrap of said split lot is delivered to an analysis device and is analysed by said device. In this way, the scrap of a split lot is examined in its entirety so that statistical uncertainties, as they occur, for instance, in a sample-based analysis, essentially do not occur.

In a further embodiment, the composition analysis comprises a spectroscopic analysis, in particular a laser-induced breakdown spectroscopy (LIBS), an X-ray fluorescence analysis (XRF) and/or a prompt-gamma neutron activation analysis (PGNAA). It was found that these methods are particularly well suited in order to analyse the entire scrap of a split lot. In the case of laser-induced breakdown spectroscopy, material is ablated from the individual scrap grains by means of a particularly pulsed laser beam and the light emitted by the ablated material is examined spectroscopically. In the case of X-ray fluorescence analysis, the material of the scrap is excited with X-ray radiation and the light emitted by the material is examined spectroscopically. In the case of the prompt-gamma neutron activation analysis, the atomic nuclei of the scrap material are excited by neutrons from a radioactive source and the gamma or X-ray radiation emitted by the atomic nuclei is examined spectroscopically. With these methods, it can thus be analysed which alloy elements are contained in what concentration in the scrap.

In a further embodiment, the item of composition information contains a value for the proportion of weight of at least one alloy component to the total weight of the analysed split lot. The value for the proportion of weight can be a relative value, for example, the content of an alloy component in weight percent, or an absolute value, for example, the content of the alloy component in kg.

In a further embodiment, the item of composition information contains a value for the weight of the split lot, for example, the weight of the split lot in kg. For this purpose, a weighing of the split lot can in particular be carried out before, after or during the composition analysis. If, for example, the scrap of the split lot is transported by means of a conveyor belt to the analysis device, then the scrap weight can be determined via a belt weigher. The value for the weight of the split lot is useful, in particular, for the decision in which way the respective split lot can be used further.

In a further embodiment, the split lots are assigned in each case to one of a plurality of classes as a function of the respectively assigned item of composition information and a predetermined assignment rule. In this way, a classification of the split lots is achieved by means of the respective composition, so that the individual split lots can be used in a more targeted manner, for example, in order to produce products of a specific alloy composition. The assignment to a class can, for example, be performed by means of a computer.

In a further embodiment, only such split lots are assigned to a first class, the value of which for the proportion of weight of at least one alloy component lies in a predetermined range for said alloy component. For example, a first class can be defined by an upper limit value for a specific alloy element, for example, Mg. The item of composition information for this purpose contains preferably a value for the content of the specific alloy element. If the content of the alloy element is below the limit value predetermined by the class, then the respective split lot is assigned to this class. If the content of the alloy element, on the contrary, is above the limit value predetermined by the class, then the split lot is not assigned to this class, but, if appropriate, to another class.

In a further embodiment, the split lots are assigned in each case to one of a plurality of predetermined alloy specifications as a function of the respectively assigned item of composition information. In the production operation, it is frequently known which alloys are processed during the operation. It can therefore be expected that the scraps accruing in the production operation do not have just any alloy, but rather one of the known alloys used in the operation. This information is utilised in the present embodiment in order to achieve a better analysis of the split lots. For this purpose, the alloys used in a production operation can be predetermined as alloy specifications. An analysed split lot can then be assigned to that alloy specification, the composition of which matches the item of composition information of the split lot. If the item of composition information of a split lot indicates, for example, a particularly low Mg content, then the respective split lot can be assigned to an alloy specification with low Mg content if the remaining alloy specifications require higher Mg contents.

In a further embodiment, one or a plurality of split lots with a predetermined target range for at least a first alloy component are selected from a plurality of split lots, wherein the selection is performed in that split lots are assigned component to one of a plurality of predetermined alloy compositions as a function of their respective content of at least a second alloy component and are selected only if the first alloy component of the predetermined alloy composition assigned to the respective split lot lies within the target range predetermined for the first alloy component. The target range of an alloy component is understood to mean the range, in which the content of the respective alloy component should lie for a selected split lot.

This embodiment is particularly suitable for selecting split lots for the production of an alloy, wherein the alloy has requirements for an alloy component that can be controlled poorly or not precisely enough with an analysis device, for example, because the required maximum content of the respective alloy component lies below the detection limit. In the case of the present embodiment, the suitable split lots are not determined directly via the first alloy component which component is difficult to control, but rather indirectly via a better detectable second alloy component. This is particularly possible by utilising the additional information about the alloy compositions that are present in principle. In a production operation, the alloy compositions of the processed products are typically known, so that the accruing scrap must be assigned only to one of said alloy compositions in order to determine the composition of the scrap. Thus, by means of characteristic contents of specific (second) alloy components the associated alloy can be deduced and via the known composition of the associated alloy in turn the content of a specific (first) alloy component can be deduced, which (first) alloy component is itself difficult to measure.

In a further embodiment, split lots assigned to a predetermined class or a predetermined alloy composition are combined to form a large lot. In this way split lots which are similar or the same with respect to their composition can be combined in a targeted way, in order then to be stored or transported economically due to the larger lot size.

In a further embodiment, the plurality of separated split lots is provided by dividing a large lot into a plurality of split lots. The large lot can, for example, have a weight of more than 20 tonnes, in particular more than 25 tonnes. If, for example, a large lot of scrap of 25 tonnes, for example a large delivery of scrap, should be prepared for a recycling, then this large lot can be divided, for example, into five parts of 5 tonnes each. The five split lots are then subjected in each case to a composition analysis according to the described method. In this way, large lots, in which scraps of different alloys can be mixed, can be broken down into split lots, the composition of which is then practically completely known in each case through the composition analysis. The size of the split lots is preferably adapted to the batch process since large lots are rarely supplied to a smelting furnace as a whole.

The division of a large lot into a plurality of split lots is particularly advantageous when the scrap of the large lot is very inhomogeneous. If the scrap of the large lot contains, for example, an engine block with a strongly Cu-containing alloy, then the Cu content of the large lot is locally very strongly concentrated. If, without division into split lots and composition analysis, simply a part was taken from the large lot and supplied to a smelting furnace, then the Cu content of the removed part would depend significantly on whether the removed part comprises the engine block or not. The uncertainty with respect to the Cu content would therefore be very large in this approach. By means of the division into split lots and the practically complete analysis of the split lots (instead of only sample analysis) the uncertainty about the composition of the individual split lots can be considerably reduced.

In a further embodiment, for the production of an alloy with predetermined specification, a subset of suitable split lots is selected from a plurality of split lots, each of said split lots of the plurality of split lots having an assigned item of composition information, for the alloy composition to be obtained as a function of the composition information items assigned to the split lots and of the predetermined specification.

In this way, an optimised target batch for the production of an alloy can be provided using as much scrap as possible. Computer algorithms for the batch optimisation are in principle known. However, their application until now has been problematic due to the high uncertainties with regard to the composition of the scrap. With the division of the scrap into split lots and the assigned, reliable composition information such a batch optimisation can be carried out significantly more reliably with the described method.

In a further embodiment, the split lots are stored for random access until the selection for the production of an alloy with predetermined specification for the alloy composition to be obtained. In this way, the individual split lots can be removed depending on their composition in a targeted way and supplied to a specific use. The storage of the split lots can, for example, be carried out in individual scrap containers in a shelf storage system.

Further features and advantages of the invention result from the following description of several exemplary embodiments, wherein reference is made to the attached drawing.

DETAILED DESCRIPTION OF THE INVENTION

Figure 1:
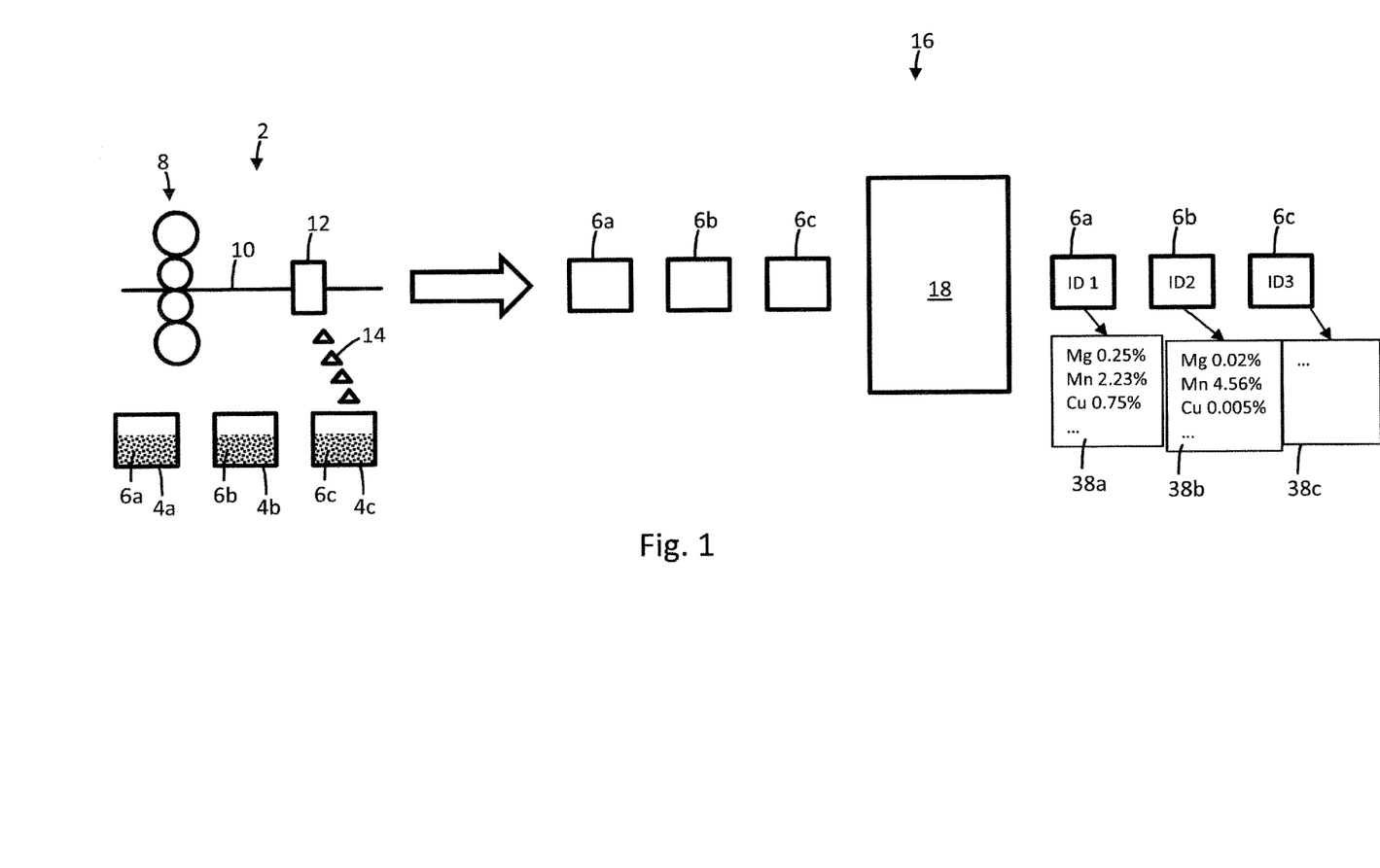
FIG. 1 shows a first exemplary embodiment of the method according to the present invention.

FIG. 1 shows a first exemplary embodiment of the method according to the present invention. In the method, aluminium scrap accruing during a production operation 2 is filled into several scrap containers 4a-c and in this way is provided in the form of a plurality of split lots 6a-c separated from one another. In FIG. 1, only three split lots 6a-c are exemplarily shown, while in a production operation 2 typically a significantly larger number of split lots is provided.

In the present example, the production operation 2 is a rolling operation (symbolized in FIG. 1 by roll stand 8) for the production of aluminium strips 10. In such a rolling operation, inter alia, trimming scraps 24 accrue at the trimming shears 12 when edge trimming rolled strips 10. The initially empty scrap containers 4a-c are provided at the trimming scraps 24 and then, one after the other, filled with scrap 14 up to a predetermined weight of for example 2 tonnes.

In the rolling operation, typically products made from different alloys are rolled one after the other. When the alloy is changed, this can lead to scraps 14 made from different alloys passing into one scrap container if the scrap container is not changed precisely during the transition from a rolled product of one alloy to a rolled product of another alloy at the trimming shears 12.

It was found that an only sample-based examination of the scraps in the split lots leads to large statistical inaccuracies, since the actual composition of the scraps partly deviates significantly from the sample-based analysis. In melting aluminium, a crucible could in the past therefore be filled only approximately to 80% with scraps and be melted. After the melting, a chemical analysis of the melt was then required, in order to determine the actually present composition of the alloy. This frequently deviated significantly from the composition calculated from the sample-based analyses of the scraps, so that the remaining 20% of the crucible filling had to be filled in a defined manner for correcting the alloy composition.

This problem is overcome in the present case in that the scraps are provided in split lots, whereby a targeted selection of defined scrap amounts is made possible for the melting, and otherwise a composition analysis is carried out for each split lot.

Accordingly, in the exemplary embodiment in FIG. 1 after the provision of the split lots 6a-c a composition analysis is carried out in an analysis step 16. For this purpose, the containers 4a-c with the split lots 6a-c are supplied separately from one another to an analysis device 18, with which the composition of the scraps of the split lots 6a-c can be analysed.

Figure 2:
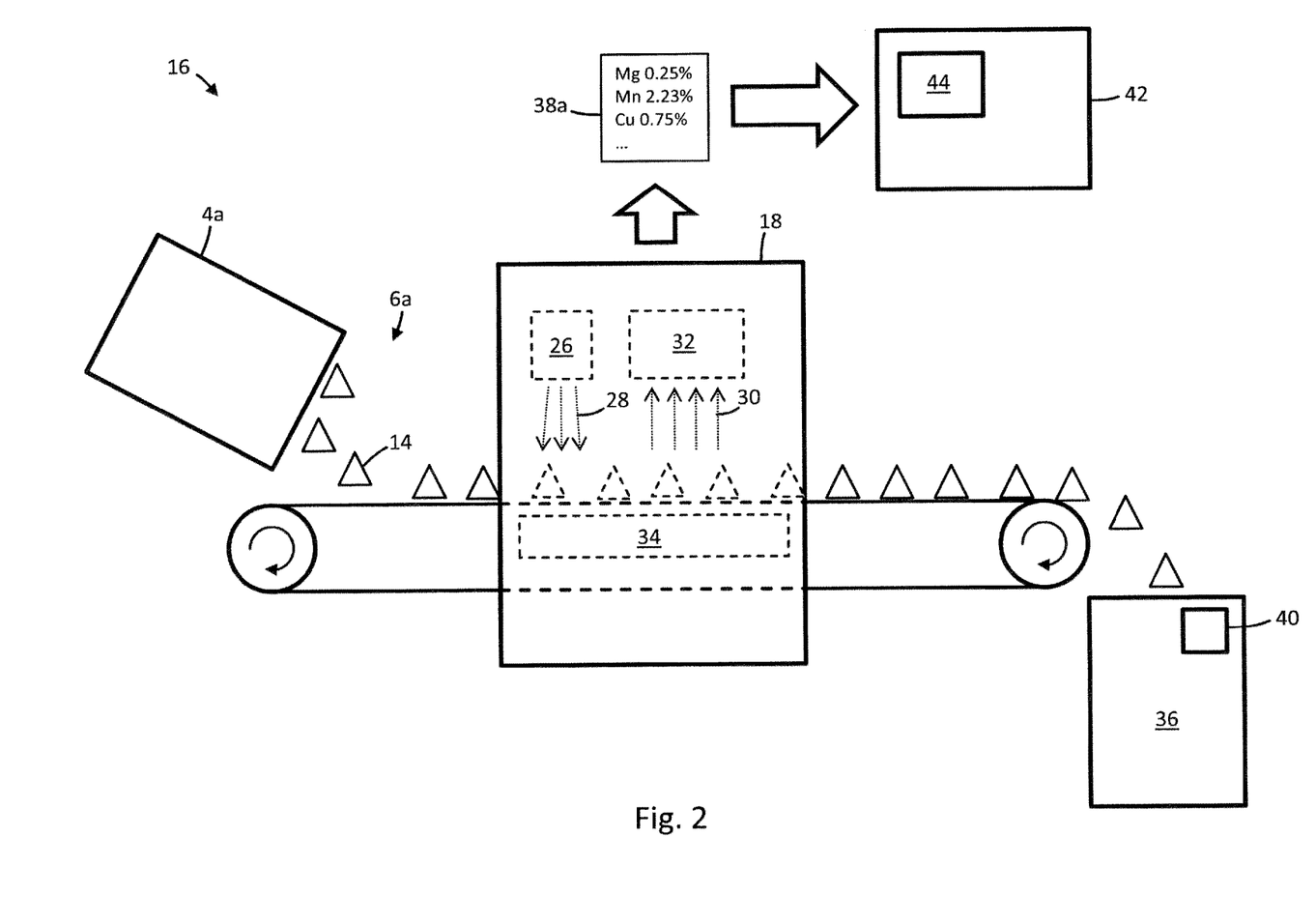
FIG. 2 shows a composition analysis step for the method from FIG. 1.

FIG. 2 shows an example for such an analysis step 16. The content of the scrap container 4a, that is, the scrap 14 of the split lot 6a, is given, preferably uniformly, on a conveyor belt 22 and then transported successively through an analysis device 18. The analysis device 18 is in this example an analysis device for the prompt-gamma neutron activation analysis (PGNAA). For this purpose, the analysis device 18 has a neutron source 26, for example, a suitable radioactive nuclide such as $^{252}$Cf, which provides neutrons 28, to which the scrap 14 is subjected. The neutrons 28 lead to an excitation of the atomic nuclei in the scrap 14 so that the atomic nuclei emit X-rays 30 with a spectrum typical for the respective element. By the analysis of the X-rays 30 in a spectrometer 32, the elements contained in the scrap as well as their content can thus be deduced. The analysis device 18 furthermore also has a belt weigher 34, by means of which the weight of the scrap 14 from the split lot 6a can be determined. From the analysis result of the spectrometer 32 and the belt weigher 34 the analysis device 18 can reliably determine the relative and absolute content of an alloy element in the split lot 6a. The reliability of the analysis result is achieved in particular in this type of analysis by analysing practically the entire scrap amount of the split lot 6a and not only a small fraction as in the sample-based analysis.

After the analysis in the analysis device 18, the scrap 14 is transported via the conveyor belt 22 to the scrap container 36 and is stored in said container separately until further use. In particular, initially no mixture of different split lots 6a-c occurs. An item of composition information 38, which is based on the analysis result of the analysis device 18, is assigned to the split lot 6a collected again in the scrap container 36. The item of composition information 38a can, for example, contain values for absolute or relative content of specific alloy elements of the split lot 6a and the weight of the split lot 6a. An identification 40 is assigned to the scrap container 36, which contains the split lot 6a, for the assignment of the item of composition information. This identification 40 is, for example, applied to the scrap container 36 as a barcode or the like. In FIGS. 1 and 3 to 5, said identification 40 respectively assigned to the split lots is symbolised by the label "ID1", "ID2", "ID3", etc.

The item of composition information 38a and the identification 40 are transmitted to a data processing system 42 connected to the analysis device 18. The latter links the identification 40 to the item of composition information 38a of the split lot 6a, for example, by storing a table in the memory 44 of the data processing system 42, in which table the identification 40 is stored together with the item of composition information 38a.

The analysis step 16 depicted in FIG. 2 is carried out in the exemplary embodiment from FIG. 1 for all split lots 6a-c, so that after this step an according item of composition information 38a-c is assigned to each split lot 6a-c.

As a result of the fact that at the end of the method from FIG. 1 an according and particularly reliable item of composition information 38a-c is assigned to each split lot 6a-c, the split lots 6a-c can now be selected in a targeted manner for the suitable use.

Figure 3:
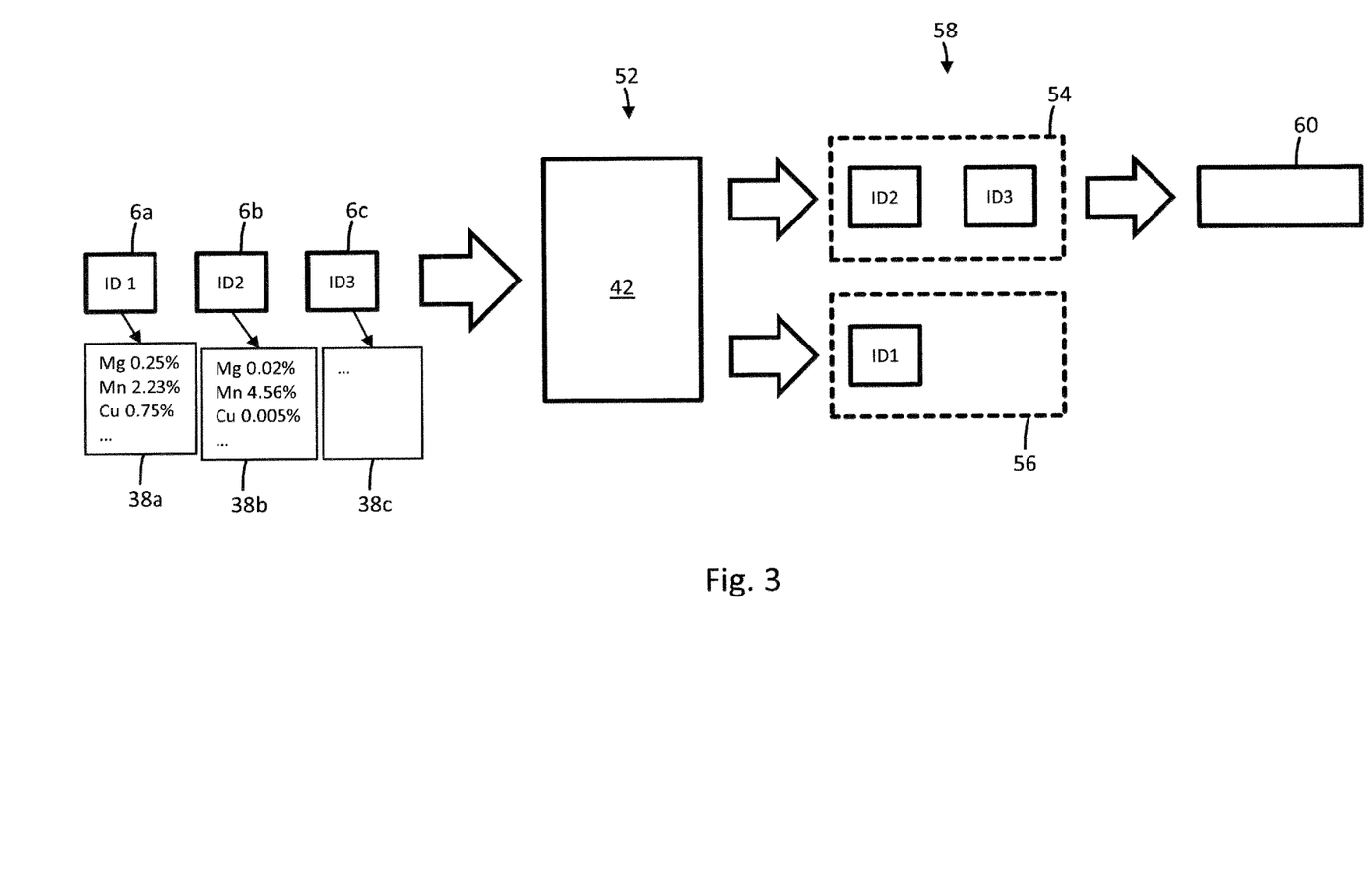
FIG. 3 shows a second exemplary embodiment of the method according to the present invention.

FIG. 3 shows an exemplary embodiment of the method, in which the split lots 6a-c are divided for a specific use into different classes via the composition information 38a-c. The method of this exemplary embodiment comprises initially the steps depicted in FIG. 1 of the provision of the amount of aluminium scrap in split lots 6a-c and of the composition analysis as well as of the assignment of the composition information 38a-c to the respective split lots 6a-c.

In the subsequent step 52, the split lots 6a-c are assigned in each case to one of a first class 54 and a second class 56 as a function of the respectively assigned item of composition information 38a-c and a predetermined assignment rule. In the example, said assignment takes place in step 52 initially with the data processing system 42.

The assignment rule is defined in this example such that split lots with a Mg content of max. 0.1 wt.-%. are assigned to the first class 54 and split lots with a Mg content of more than 0.1 wt.-% are assigned to the second class. In this way, split lots can be selected in a targeted manner for the production of a low Mg alloy by selecting only split lots from the first class for this purpose.

The assignment of the respective class to the individual split lots can initially take place in the memory 44 of the data processing system 42. In a further step 58, the appropriate split lots 6a-c or the scrap containers, in which the split lots 6a-c are stored, can be provided with an appropriate identification. Furthermore, the split lots of a class can also be assigned to one another spatially, by storing the split lots arranged according to their classes. It is also conceivable to combine several or all split lots of one class to form a large lot 60. Thus, the split lots 6b and 6c of the first class 54 can be filled into a common scrap container and then, for example, sold to an aluminium smelting plant or be directly melted.

Figure 4:
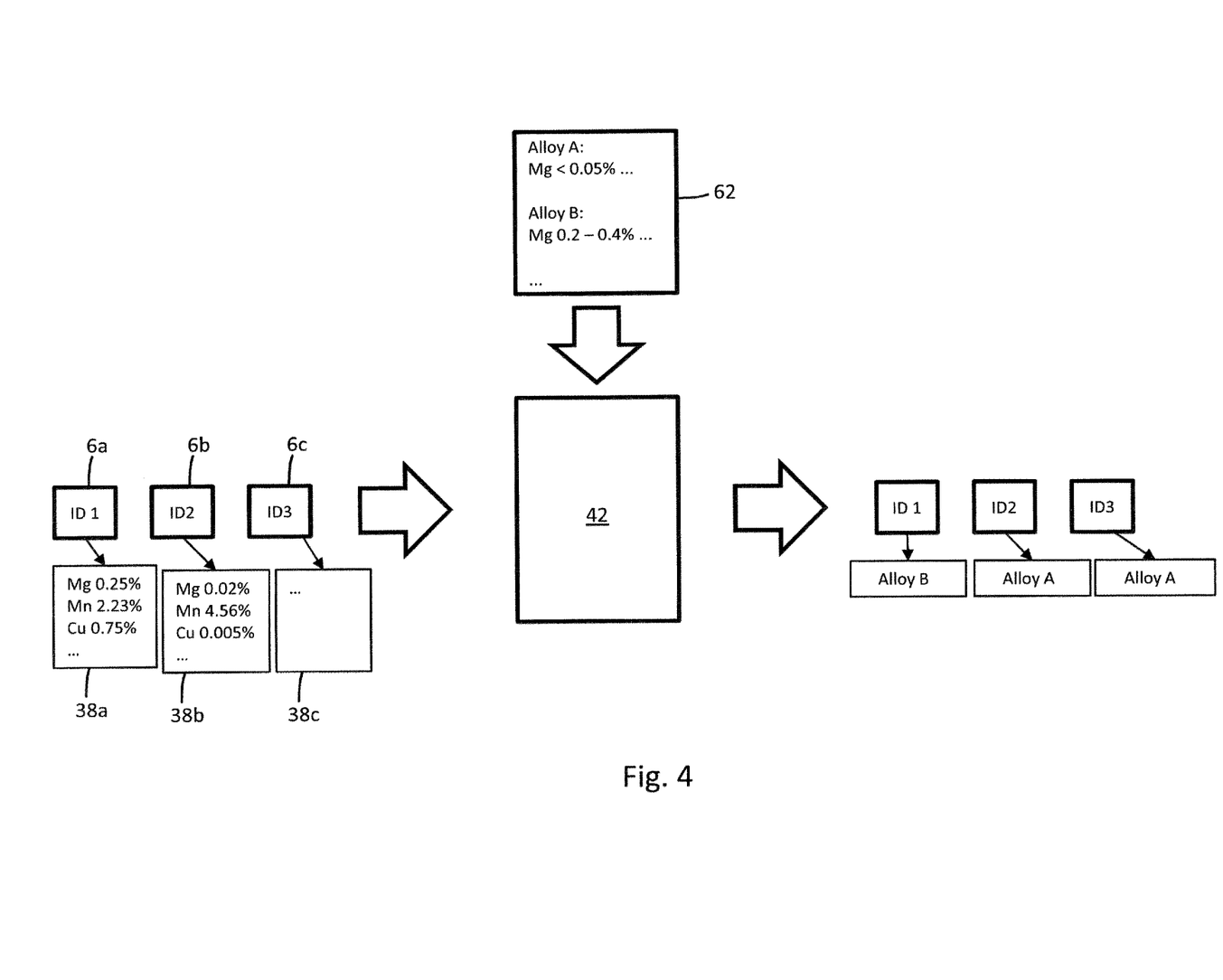
FIG. 4 shows a third exemplary embodiment of the method according to the present invention.

FIG. 4 shows a further exemplary embodiment of the method, in which the split lots 6a-c are assigned via the composition information items 38a-c as well as a data set 62 with predetermined alloy specifications in each case to an alloy specification. The method of this exemplary embodiment initially comprises the steps depicted in FIG. 1 of the provision of the amount of aluminium scrap in split lots 6a-c and of the composition analysis as well as of the assignment of the composition information 38a-c to the respective split lots 6a-c.

The alloy specifications of the alloys processed in the production operation 2 are typically known. It has been recognised that said item of information can be used advantageously for analysis of the split lots 6a-c.

For this purpose, the alloy specifications of the alloys processed during the production operation 2 are compiled in a data set 62, wherein the data set for each of the alloy specifications (alloy A, alloy B, etc.) contains information on the range limits of specific alloy elements (e.g. Si, Fe, Mn, Mg, etc.). The data set is stored in the memory 44 of the data processing system 42.

The data processing system 42 is designed to match composition information items 38a-c with the range limits of the alloy elements of the individual alloys A, B, etc., and to assign the split lots 6a-c to the respective matching alloy. In the best case, the assignment is unambiguous, so that the respectively processed item of composition information matches only precisely one alloy from the data set. If several alloys from the data set match the item of composition information, then a rule is implemented in the program of the data processing system 42, which determines to which of these several alloys the appropriate split lot is assigned.

In the example depicted in FIG. 4, the specification of the alloy A requires, for example, a Mg content of <0.05%, while the remaining alloys in the data set 62 require a higher Mg content. In this case, for example, the split lot 6b can clearly be assigned to the alloy A.

The assignment can in turn take place by saving a link of the identification 40 of the split lot to the assigned alloy in the memory 44 or by application of an appropriate identification with the assigned alloy to the appropriate split lot or to the associated scrap container.

The assignment of known alloys to the individual split lots permits a better analysis, since previously known information can be used in the analysis. In particular, this approach also permits the reliable classification of split lots for the production of alloys with limits for specific alloy elements, which lie below the detection threshold of the analysis device 18.

For example, if split lots with particularly low Mg content are wanted, which have a Mg content below the detection threshold, and if it is known that such low Mg contents only occur in the case of an alloy which has a characteristic Mn content, then the split lots of the appropriate alloy with the characteristic Mn content and consequently with the desired low Mg content can be selected via an assignment of the split lots to predetermined alloys via the Mn content. This approach thus permits the selection of alloys with specific requirements for a first alloy element (here Mg) by an assignment via a second alloy element (here Mn) which can be better detected.

Figure 5:
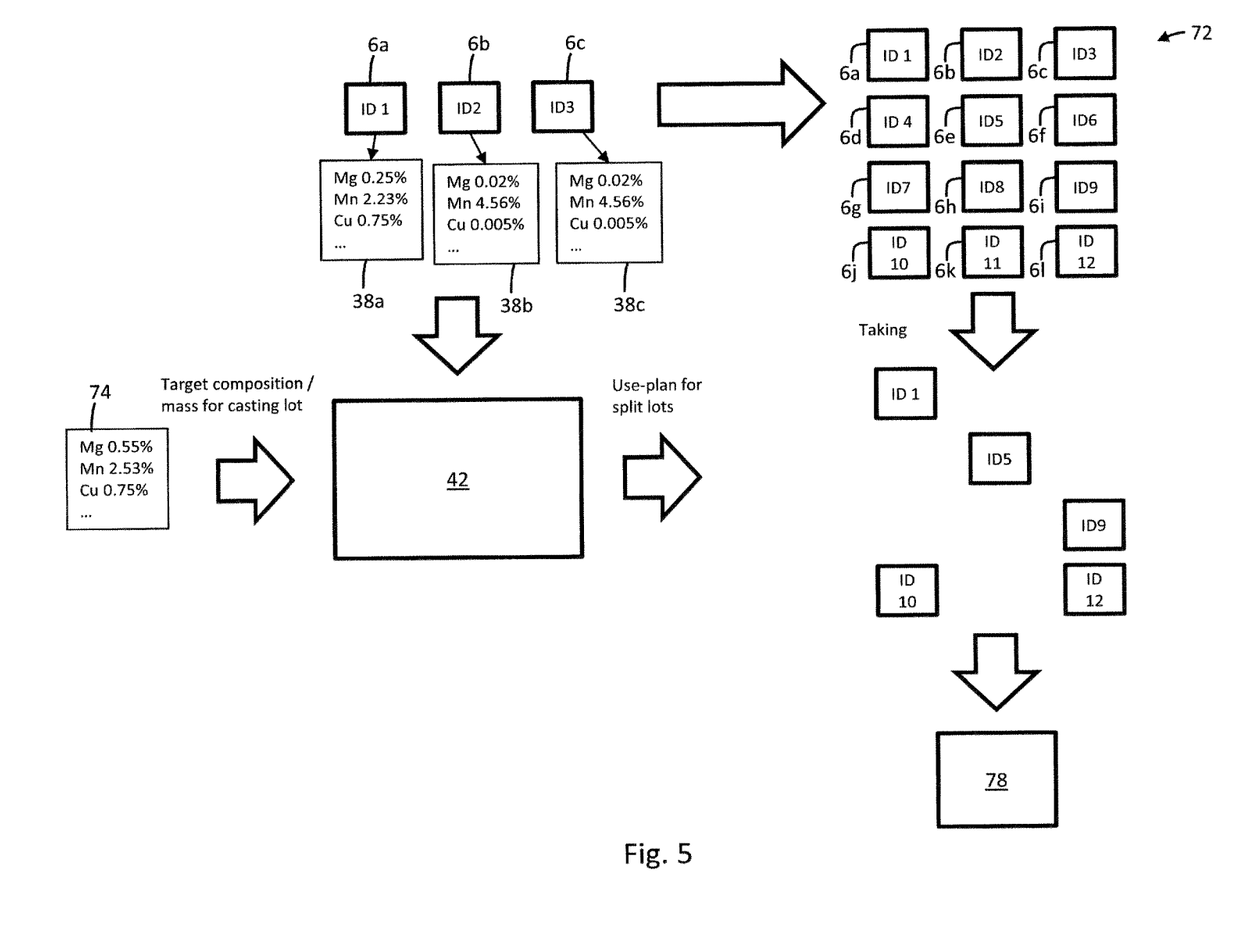
FIG. 5 shows a fourth exemplary embodiment of the method according to the present invention.

FIG. 5 shows a further exemplary embodiment of the method in which the split lots 6a-c are selected via the composition information items 38a-c in a targeted manner for the production of a predetermined target alloy. The method of this exemplary embodiment initially comprises the steps depicted in FIG. 1 of the provision of the amount of aluminium scrap in split lots 6a-c and of the composition analysis as well as of the assignment of the composition information items 38a-c to the respective split lots 6a-c.

The split lots 6a-c are stored separately accessible in a store 72, which has further split lots 6d-1 to which an appropriate item of composition information 38d-1 is also assigned. The composition information items 38a-1 are stored in the memory 44 of the data processing system 42.

In order to produce a specific alloy with a predetermined alloy specification 74, the alloy specification 74 with the desired weight is transmitted to the data processing system 42. By using software for batch optimisation, the data processing system 42 determines a selection or subset 76 of the split lots 6a-1, which have the suitable alloy elements in the suitable contents and with the suitable weight, from the desired alloy specification 74 and the composition information items 38a-1, which in addition to the respective composition also include a value for the respective weight of the individual split lots. This selection or subset 76 of the split lots 6a-1 can then be taken from the store 72 and be combined, for example, to form a large lot 78 that can then be delivered to a smelting plant or be melted directly.

In this way, an optimised target batch with maximum scrap use can be achieved for the production of a predetermined alloy. In particular, the smelting crucible can be filled in this way completely or nearly completely with scrap, in order to obtain the desired alloy.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for recycling metal scraps, comprising the steps of:
    providing an amount of metal scrap in the form of a plurality of separated split lots, wherein the separated split lots are provided in the form of individual packages;
    carrying out, for each split lot, a composition analysis and assigning an item of composition information based on said composition analysis to the respective split lot that has been analysed; and
    selecting, for the production of an alloy with predetermined specification, a subset of suitable split lots from a plurality of split lots, each of said split lots of the plurality of split lots having an assigned item of composition information, for the alloy composition to be obtained as a function of the composition information items assigned to the split lots and of the predetermined specification.

2. The method according to claim 1, wherein the composition analysis of a split lot is carried out in that the entire scrap of said split lot is delivered to an analysis device and is analysed by said device.

3. The method according to claim 1, wherein the composition analysis comprises a spectroscopic analysis.

4. The method according to claim 1, wherein the item of composition information contains a value for the proportion of weight of at least one alloy component to the total weight of the analysed split lot.

5. The method according to claim 1, wherein the item of composition information contains a value for the weight of the split lot.

6. The method according to claim 1, wherein the split lots are assigned in each case to one of a plurality of classes as a function of the respectively assigned item of composition information and a predetermined assignment rule.

7. The method according to claim 6, wherein only such split lots are assigned to a first class, the value of which for the proportion of weight of at least one alloy component lies in a predetermined range for said alloy component.

8. The method according to claim 1, wherein the split lots are assigned in each case to one of a plurality of predetermined alloy specifications as a function of the respectively assigned item of composition information.

9. The method according to claim 1, further comprising the step of selecting one or a plurality of split lots with a predetermined target range for at least a first alloy component from the plurality of split lots, wherein the selection is performed in that split lots are assigned to one of a plurality of predetermined alloy compositions as a function of their respective content of at least a second alloy component and are selected only if the first alloy component of the predetermined alloy composition assigned to the respective split lot lies within the target range predetermined for the first alloy component.

10. The method according to claim 6, wherein split lots assigned to a predetermined class or to a predetermined alloy composition are combined to form a large lot.

11. The method according to claim 1, further comprising the step of storing the split lots for random access until the selection for the production of an alloy with predetermined specification for the alloy composition to be obtained.

12. The method according to claim 1, wherein the plurality of separated split lots is provided by dividing a large lot into a plurality of split lots.

13. The method according to claim 3, wherein the spectroscopic analysis comprises a laser-induced breakdown spectroscopy (LIBS), an X-ray fluorescence analysis (XRF) and/or a prompt-gamma neutron activation analysis (PG-NAA).

14. The method according to claim 1, wherein the metal scrap is aluminium scrap.

* * * * *